US00PP08913P

United States Patent [19]

Zaiger et al.

[11] Patent Number: Plant 8,913

[45] Date of Patent: Sep. 27, 1994

[54] INTERSPECIFIC ROOTSTOCK TREE "ATLAS"

[76] Inventors: Chris F. Zaiger, 537 Rosemore Ave.; Gary N. Zaiger, 1907 Elm Ave.; Leith M. Gardner, 1207 Grimes Ave.; Grant G. Zaiger, 4005 California Ave., all of Modesto, Calif. 95358

[21] Appl. No.: 183,352

[22] Filed: Jan. 19, 1994

[51] Int. Cl.[5] ..... A01H 5/00

[52] U.S. Cl. ..... Plt./43.1

[58] Field of Search ..... Plt. 42.1, 43.1

*Primary Examiner*—James R. Feyrer

[57] ABSTRACT

A new and distinct interspecific rootstock variety, its novelty consists of the following unique combination of features that are outstanding in a new rootstock variety:

1. The ability to produce roots from dormant hardwood cuttings when planted directly into the field.
2. Rapid initiation of roots facilitates early spring budding in nursery.
3. Vigorous upright growth with little to no root suckering.
4. Has scion compatibility with peaches and nectarines.
5. Heavy and regular fruit production of the scion variety.
6. A well anchored deep root system.

1 Drawing Sheet

ORIGIN OF THE VARIETY

The present new interspecific rootstock tree was developed by us in our experimental orchard located near Modesto, Calif. as a first generation cross between the rootstock variety Nemaguard (non-patented) and a selected seedling with the field identification number of 14H528. The pollen parent 14H528 originated from a cross between Jordanola Almond (non-patented) and Prunus blierianna. We grew and maintained a large group of these first generation seedlings under careful observation, during which time the present variety exhibited strong, upright growth and was selected for asexual propagation.

ASEXUAL REPRODUCTION OF THE VARIETY

The new and distinct rootstock variety was asexually propagated by cuttings and budding, as performed by us in our experimental orchard located near Modesto, Calif. and shows that all characteristics are established and transmitted through succeeding propagations and come true to the original tree in all respects.

SUMMARY OF THE VARIETY

The present variety of interpsecific rootstock tree is of large size, vigorous upright growth with little to no suckering and the dormant cuttings from this tree have the ability to root when planted directly into the field. The new rootstock is compatible with scion varieties of peach and nectarine and are well anchored with a deep root system. In comparison to the rootstock Nemaguard (non-patented) which is propagated from seed, the new interspecific rootstock can be budded earlier in the nursery and upon maturity the scion variety is approximately 25% larger in size, has larger size fruit with greater fruit production, the fruit is approximately 3 to 4 days later in maturity.

PHOTOGRAPHS OF THE VARIETY

The accompanying color photographs show reproductions of the foliage and fruit of the new interspecific variety of rootstock tree. The illustrations are of the upper and lower surface of the leaves, an exterior and sectional view of the fruit divided in the suture plane. The photographs were taken shortly after being picked (soft ripe) and the colors are as nearly true as reasonably possible in a color representation of this type.

DESCRIPTION OF THE VARIETY

The following is a detailed botanical description of the new and distinct variety of interspecific rootstock tree, its flowers, fruit and foliage, as based on observations of specimens grown near Modesto, Calif. with color terminology (except those in common terms) in accordance with Reinhold Color Atlas by A. Kornerup and J. H. Wanscher.

Tree:
- *Size.*—Large.
- *Vigor.*—Vigorous.
- *Growth.*—Upright.
- *Density.*—Medium dense.
- *Bearer.*—Regular.
- *Production.*—Productive.

Trunk:
- *Size.*—Large.
- *Texture.*—Medium shaggy.
- *Color.*—Grayish brown to brown (5-E-4) to (5-E-5).

Branches:
- *Size.*—Medium.
- *Texture.*—Smooth to medium rough.
- *Lenticels.*—Large size. Medium number.
- *Color.*—Linoleum brown to light brown (5-E-7) to (5-E-8).

Leaves:
- *Size.*—Large. Average length — $7\frac{1}{8}''$. Average width — $1\frac{5}{8}''$.
- *Form.*—Lanceolate.
- *Margin.*—Crenate.
- *Thickness.*—Medium.
- *Petiole.*—Average length — 9/16". Medium thickness.
- *Surface.*—Smooth.
- *Glands.*—Reniform. Number varies from 2 to 6. Average nubmer 4. Medium to large size. Located on base of leaf blade and upper portion of petiole.

*Color.*—Upper surface —green to dark green (27-F-6) to (27-F-7). Lower surface — grayish green to green (28-E-6) to (28-E-7).

Flower buds:

*Size.*—Medium.

*Length.*—Medium.

*Form.*—Plump.

*Pubescence.*—Pubescent.

Flowers:

*Size.*—Medium, non-showy.

*Blooming period.*—Mar. 2, 1993 to Mar. 10, 1993. Varies slightly with climatic conditions.

*Pollen.*—Present.

*Color.*—Pink.

Fruit:

*Maturity when described.*—Soft Ripe — Aug. 22, 1993.

*Size.*—Medium. Average diameter axially — $2\frac{1}{4}''$ to $2\frac{1}{2}''$. Average transversely in suture plane — $2\frac{1}{4}''$ to $2\frac{1}{2}''$.

*Form.*—Nearly globose, majority of fruit slightly enlarged at apex.

*Suture.*—Pronounced, extends from base to apex.

*Ventral surface.*—Slight depression, lipped.

*Apex.*—Slightly enlarged, rounded over pistil area.

*Base.*—Retuse.

*Cavity.*—Rounded, slightly elongated in suture plane. Average depth — $\frac{1}{2}''$. Average breadth — $\frac{5}{8}''$.

Flesh:

*Ripens.*—Evenly.

*Texture.*—Soft.

*Fibers.*—Moderate number.

*Amygdalin.*—Moderate.

*Aroma.*—Lacking.

*Eating quality.*—Very poor.

*Flavor.*—Poor.

*Color.*—Pale — yellowish white (2-A-2) to (2-A-3). Pit Cavity — yellowish white to yellowish gray — (2-A-2) to (2-B-2).

Skin:

*Thickness.*—Medium.

*Texture.*—Medium, tenacious to flesh.

*Down.*—Moderate to heavy, medium length.

*Tendency to crack.*—None.

*Color.*—Yellowish white to pale yellow (3-A-2) to (3-A-3).

Stone:

*Type.*—Clingstone.

*Size.*—Medium to large. Average length — $1\frac{3}{8}''$. Average breadth — 1 1/16″. Average thickness — $\frac{1}{2}''$.

Form.—Ovoid.

*Base.*—Rounded, varies from rounded to straight.

*Apex.*—Acuminate.

*Sides.*—Equal to unequal.

*Surface.*—Small irregular furrows toward apex, pitted toward base, ridges usually rounded and pit cavities vary from round to slightly elongated.

*Tendency to split.*—None.

Use: Fruit has no commercial value. Colonal rootstock propagated by dormant cuttings.

The present interspecific rootstock tree, its flowers and fruit herein described may vary in slight detail due to climatic, soil conditions and cultural practices under which the variety may be grown. The present description is that of the tree grown under the ecological conditions prevailing near Modesto, Calif.

We claim:

1. A new and distinct interspecific rootstock tree, substantially as illustrated and described, characterized by its large size, vigorous upright growth, having the ability to be asexually reproduced by cuttings when planted directly into the field and developing a well anchored, deep root system; in comparison to scions budded on the Nemaguard rootstock, the scion variety is approximately 25% larger in size, having greater fruit production with larger size fruit.

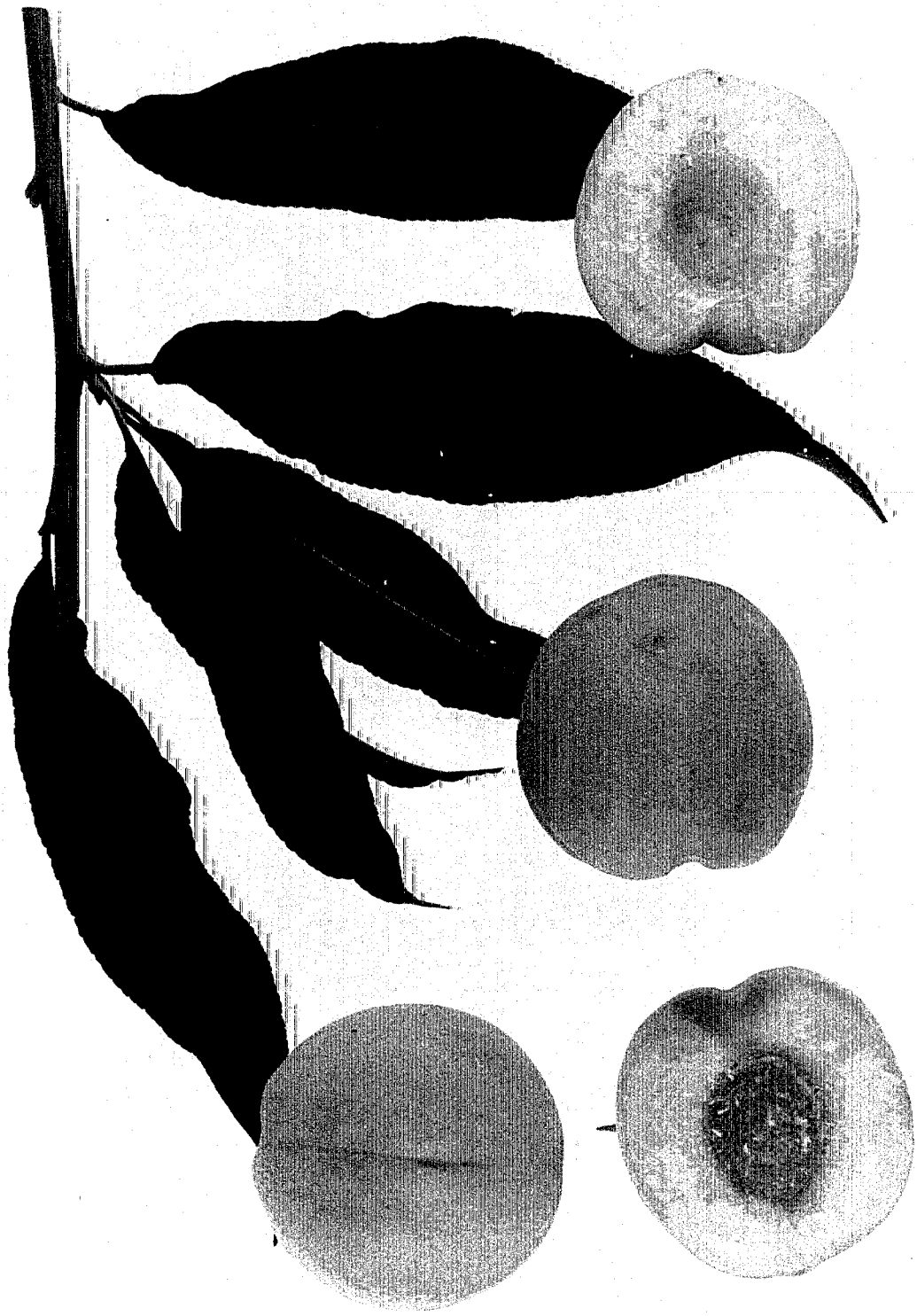

* * * * *